United States Patent [19]
Strauss et al.

[11] Patent Number: 6,130,357
[45] Date of Patent: Oct. 10, 2000

[54] POLYHALOGENATED MONOHETEROBORANE ANION COMPOSITIONS

[75] Inventors: Steven H. Strauss; Sergei V. Ivanov; Anthony J. Lupinetti, all of Fort Collins, Colo.

[73] Assignee: Colorado State University Research Foundation, Ft. Collins, Colo.

[21] Appl. No.: 09/049,420

[22] Filed: Mar. 27, 1998

Related U.S. Application Data

[60] Provisional application No. 60/043,041, Apr. 3, 1997, and provisional application No. 60/058,836, Sep. 11, 1997.

[51] Int. Cl.$^7$ ........................................................ C07F 5/02
[52] U.S. Cl. .......................... 568/3; 568/5; 568/2; 556/7; 556/8; 564/8
[58] Field of Search ............................ 568/3, 2, 5; 556/7; 556/8; 564/8

[56] References Cited

U.S. PATENT DOCUMENTS

| | | | |
|---|---|---|---|
| 3,551,120 | 12/1970 | Miller et al. | 23/358 |
| 3,567,410 | 3/1971 | Young . | |
| 5,731,470 | 3/1998 | Michl | 564/9 |

FOREIGN PATENT DOCUMENTS 0 277 003 A1   1/1988   European Pat. Off. .

OTHER PUBLICATIONS

CA: 126:59993 abs of "Reactions of CB9H10 with Electrophiles" Strauss, Inorg Chem 35 (26) pp.7882–7891, Dec. 1996.
CA:123:98179 abs of JP07134286, May 1993.
CA:67:12206 abs of"Some new polymeric semiconductors", by Paushkin, J Polymer Sci Polym Chem Ed 5 (6) pp. 1203–20, 1967.
CA:66:29629 abs if "Pract applications of inorgnic polymers", by Parker, Dan Geol Unders Raekke, 1, 25 (2) pp. 353–6, 1965.
Strauss, "The Search for Larger and More Weakly Coordinating Anions," *Chem. Rev.*, 1993, 93, 927–942.
Regioselective Fluorination of $CB_{11}H_{12}^-$, $CB_9H_{10}^-$, and $B_{10}H_{10}^{2-}$, by Ivanov et al. in Advances in Boron Chemistry, Siebert ed., The Royal Society of Chemistry, Cambridge, UK, 1997, pp. 430–433.
"Syntheses and Reactions of Silaboranes," by Wesemann et al. in Advances in Boron Chemistry, Siebert ed., The Royal Society of Chemistry, Cambridge, UK, 1997, pp. 422–425.
"Reactivity of the Closo–Azaboranes $RNB_9H_9$ and $RNB_{11}H_{11}$," by Dirk et al. in Advances in Boron Chemistry, Siebert ed., The Royal Society of Chemistry, Cambridge, UK, 1997, pp. 399–408.

Ivanov et al., "Reactions of $CB_9H_{10}^-$ with Electrophiles, Including the Regioselective Mono–and Dihalogenation of the Lower Belt," *Inorg. Chem.*, 1996, 35, 7882–7891.
Ivanov et al., "Regioselective Fluorination of $CB_{11}H_{12}^-$. New Weakly Coordinating Anions," *Inorg. Chem.*, 1995, 34, 6419–6420.
Kongpricha et al., "Icosahedral Carboranes. XII. Direct Fluorination of o–, m–, and p–Carborane," *Inorg. Chem.*, 1969, 8, 2449–2452.
Leites et al., "Vibrational Spectra of F–substituted carbaboranes with B–F bonds," *Organomet. Chem. in the USSR*, 1991, 4, 526–529.
Lagow et al., "The synthesis of perfluoro m–caborane by direct fluorination," *J. Inorg. Nucl. Chem.*, 1973, 35, 2084–2085.
Mair et al., "2–Substituted Icosahedral Monocarbon Carboranes. Part 1. Synthesis via Boron Insertion." *J. Chem. Soc. Dalton Trans.*, 1993, 135–141.
Jiang et al., "Iodination Reactions of Icosahedral para–Carborane and the Synthesis of Carborane Derivatives with Boron–Carbon Bonds," *Inorg. Chem.*, 1995, 34, 3491–3498.
Bregadze, "Dicarba–closo–dodecaboranes $C_2B_{10}H_{12}$ and Their Derivatives," *Chem. Rev.*, 1992, 92, 209–223.
Stibr, "Carboranes Other than $C_2B_{10}H_{12}$," *Chem. Rev.*, 1992, 92, 225–250.
Plesek, "Potential Applications of Boron Cluster Compounds," *Chem. Rev.*, 1992, 92, 269–278.
Xie et al., "Chlorination of Icosahedral Carborane Anions. X–ray Crystal Structure of $[Me_3NH][CH_3-1-CB_{11}-Cl_{11}]$," *Inorg. Chem.*, 1997, 36, 2246–2247.
King et al., "Dodecamethylcarba–closo–dodecaboranyl ($CB_{11}Me_{12}$), a Stable Free Radical," *J. Am. Chem. Soc.*, 1996, 118, 10902–10903.
King et al., "Dodecamethylcarba–closo–dodecaborate(–) Anion, $CB_{11}Me_{12}^-$," *J. Am. Chem. Soc.*, 1996, 118, 3313–3314.
Srivastava et al., "Synthesis of Highly Iodinated Icosahedral Mono–and Dicarbon Carboranes," *J. Org. Chem.*, 1996, 61, 9041–9044.
Hanusa et al., "Synthesis of Polyhedral Arsaboranes and Their Metal Derivatives," *Inorg. Chem.*, 1987, 26, 4100–4102.
"New Weakly Coordingating Anions. 2. Derivatization of the Carborane Anion $CB_{11}H_{12}^-$," by Jelinek et al., in *Inorg. Chem.*, 1993, 32, 1982–1990.

*Primary Examiner*—Gary Geist
*Assistant Examiner*—Jean F Vollano
*Attorney, Agent, or Firm*—Sheridan Ross P.C.

[57] ABSTRACT

The present invention provides compounds comprising a polyhalogenated heteroborane anion of the formula $R_aZB_bH_cF_dX_e(OR'')_f^{-1}$, and a method for producing the same. Specifically, the present invention provides compounds comprising a polyfluorinated monocarborane anion.

26 Claims, 3 Drawing Sheets

POLYHALOGENATED MONOHETEROBORANE ANION COMPOSITIONS

This application claims priority to provisional applications 60/043041 filed Apr. 3, 1997 and 60/058836, filed Sep. 11, 1997.

FIELD OF THE INVENTION

The present invention relates to compounds comprising polyhalogenated monoheteroborane anion of the formula $R_aZB_bH_cF_dX_e(OR'')_f^{-1}$, and a method for producing the same.

BACKGROUND OF THE INVENTION

A compound containing a weakly coordinating anion (i.e., an anion that coordinates only weakly with a cation) is useful in a variety of applications including as an electrolyte and a catalyst. Investigations of very reactive metal and nonmetal cations continues to spur the development of new weakly coordinating anions. See, for example, Bochmann, *Angew. Chem., Int. Ed. Engl.* 1992, 31 1181; Strauss, *Chem. Rev.* 1993, 93, 927, Strauss, *Chemtracts-Inorganic Chem.* 1994, 6,1; and Seppelt, *Angew. Chem., Int. Ed. Engl.* 1993, 32, 1025. One of the most important uses of weakly coordinating anions is to enhance the catalytic activity of metal cations. Two examples that have received considerable attention recently are metallocene-catalyzed olefin polymerization, and lithium-catalyzed Diels-Alder reactions and 1,4-conjugate addition reactions. See Turner, European Patent Appl. No. 277,004, 1988; Pellecchia et al., *Makromol. Chem., Rapid Commun.* 1992, 13, 265; DuBay et al., *J. Org. Chem.* 1994, 59, 6898; Saidi et al., *Chem. Ber.* 1994, 127, 1761; Kobayashi et al., *Chem. Lett.* 1995, 307; and Arai et al., *Angew. Chem., Int. Ed. Engl.* 1996, 15, 3776.

Useful anions must not only be weakly coordinating, they must also be stable with respect to oxidation and/or fragmentation in the presence of highly electrophilic cations. In addition, an ideal weakly coordinating anions should have a single negative charge dispersed over a large surface composed of relatively nonpolar bonds to weakly basic atoms such as hydrogen or the halogens. Weakly coordinating anions which conform to many, but not all, of these criteria include $B(Ar_f)_4^-$ ($Ar_f = C_6F_5$ or 3,5-$C_6H_3(CF_3)_2$), $CB_{11}H_{12-n}X_n^-$ (X=H or I), $CB_9H_{10-n}X_n^-$ (X=H, Cl, Br or $M(OTeF_5)_n^-$ (n=4, M=B; n=6, M=Nb, Sb)).

All of the anions mentioned above have limitations. Some are too strongly coordinating for specific applications. Some are unstable under the harsh chemical conditions where they would be employed. For example, the fluorinated derivatives of $BPh_4^-$ can react with strongly electrophilic cations, causing (i) cleavage of a C—F bond and formation of a bond between the fluorine atom and the cation or (ii) transfer of a fluoroaryl group to the cation. In either case, the cation is no longer reactive or catalytically active.

Utility of carborane monoanions containing chlorine, bromine and iodine (e.g., $CB_{11}H_6Br_6^-$ and $CB_9H_5Br_5^-$) are limited for several reasons. First, the heavier halogens containing carboranes coordinate more strongly to cations than do fluorine atoms containing carboranes. The order of coordinating ability of $HCB_{11}H_5X_6^-$ ions to the electrophilic $Si(i-Pr)_3^+$ cation is: $HCB_{11}H_5Cl_6^- < HCB_{11}H_5Br_6^- < HCB_{11}H_5I_6^-$. Therefore, the fluoro derivatives $CB_{11}H_{12-n}F_n^-$ are expected to be less coordinating than any of the known halocarboranes. Another limitation is that $CB_{11}H_6Br_6^-$ and similar anions react with strong reducing agents such as sodium metal (Na). An additional limitation is that carboranes with heavier halogen groups are much easier to oxidize than carboranes containing fluorine groups. For example, $HCB_{11}H_5Br_6^-$ is oxidatively decomposed when treated with elemental fluorine.

The anion $CB_{11}(Me)_{12}^-$ is not stable in strong acid and is easily oxidized at only 1.6 V in acetonitrile solution. The most electrophilic cations, i.e., those that require new and more weakly coordinating anions, are extremely oxidizing. Therefore, the oxidation of a weakly coordinating anion at too low oxidation potential is severe limitation in their usefulness.

Most bis(dicarbollide) complex anions have not been halogenated and none have been fluorinated. In addition, they are too strongly coordinating for most applications and are too prone to oxidation. Their stability in the presence of a strong acid is expected to be poor because they are composed of dianions (e.g., $C_2B_9H_{11}^{2-}$) surrounding a trivalent $M^{+3}$ metal ion. Dianions generally react more readily and more quickly with acids than monoanions.

Other weakly coordinating monoanions, such as $ClO_4^-$, $BF_4^-$, $PF_6^-$, $SbF_6^-$, $Al(OC(Ph)(CF3)_2)_4^-$, $Nb(OCH(CF_3)_2)_6^-$, $B(OTeF_5)_4^-$, and $Nb(OTeF_5)_6^-$, are not thermally and/or hydrolytically stable.

Other anions containing boron atoms, and anion containing a carbon atom and a cluster of boron atoms, such as carboranes (e.g., $CB_5$, $CB_9$, $CB_{11}$), are not particularly stable nor weakly coordinating because the salts formed therefrom contain at most only one fluorine atom which is bonded to a boron atom. Currently, there is no synthetic method which provides carboranes with more than one fluorine atom.

The utility of partially fluorinated carboranes (i.e., carboranes wherein more than one boron atom is fluorinated, but not all boron atoms are fluorinated) such as 7,8,9,10,11,12-$CB_{11}H_6F_6^-$ are commercially limited because other isomers having the formula $CB_{11}H_6F_6^-$ may be concominantly produced in the generation of desired partially fluorinated carboranes, such undesired isomers require costly and time consuming isolation procedures to obtain a substantially pure isomer such as 7,8,9,10,11,12-$CB_{11}H_6F_6^-$.

Therefore, there is a need for a polyfluorinated carborane anion which is weakly coordinating, and is thermally and hydrolytically stable. There is also a need for a method for producing a salt containing an isomerically enriched or a pure polyfluorinated carborane anion.

SUMMARY OF THE INVENTION

The present invention is directed to a weakly coordinating anion. Specifically, the present invention is directed to a compound comprising a polyhalogenated monoheteroborane anion of the formula $R_aZB_bH_cF_dX_e(OR'')_f^{-1}$, wherein R is selected from the group consisting of a polymer, hydrogen, halide, $C_1$–$C_{10}$ alkyl, $C_1$–$C_{10}$ cycloalkyl, $C_1$–$C_{10}$ alkenyl, $C_1$–$C_{10}$ alkynyl, and $C_4$–$C_{20}$ aryl;

Z is selected from the group consisting of C, Si, Ge, Sn, Pb, N, P, As, Sb, and Bi;

each X is independently halide;

R" is selected from the group consisting of polymer, hydrogen, $C_1$–$C_{10}$ alkyl, $C_1$–$C_{10}$ cycloalkyl, $C_1$–$C_{10}$ alkenyl, $C_1$–$C_{10}$ alkynyl, and $C_4$–$C_{20}$ aryl;

a is 0 or 1;

b is an integer from 5 to 13;

c is an integer from 0 to 12;

d is an integer from 2 to 13;

e is an integer from 0 to 11; and f is an integer from 0 to 5.

The polyhalogenated monoheteroborane anion of the present invention can have any combination of a mixture of boron-hydrogen bonds (B—H), boron-fluorine bond (B—F), boron-halogen bond (B—X), and boron-hydroxyl bond(B—OH). However, the presence of a mixture of bonds can result in number of possible isomers. Thus, it is preferred that majority of the boron atoms have similar group attachments. For example, when b is 9 or 11, it is preferred that d be 9 or 11, respectively. It should be recognized, however, since the substituent on the boron atom opposite to the heteroatom in the crystal structure (typically the last numbered boron atom) can be easily replaced with a different substituents, having d=b−1 also provides a single isomer formation.

In another particular embodiment of the present invention, the polyhalogenated monoheteroborane anion is a polyfluorinated carborane anion.

Since the polyhalogenated monoheteroborane of the present invention is weakly coordinating and is stable under a variety of conditions, it can be formulated into a variety of forms. For example, the compound of the present invention can be dissolved in a variety of solvent to provide a solution which comprises the polyhalogenated monoheteroborane anion of the present invention. Alternatively, the compound of the present invention can be heated to provide a molten salt or a liquid comprising the polyhalogenated monoheteroborane anion of the present invention. Or a gel comprising the polyhalogenated monoheteroborane anion of the present invention can be formulated by admixing the compound of the present invention with appropriate polymer or by admixing the compound of the present invention with the polymer's precursor prior to a polymerization reaction.

Another embodiment of the present invention is a method for producing a polyhalogenated monoheteroborane anion of the formula $R_aZB_bH_cF_dX_e(OR'')_f^-$ comprising the step of contacting a compound of the formula $M[R'_aZB_bH_gF_hX_i(OR'')_j]_k$ with a mixture comprising $X'_2$ and HX'; wherein M is a cation having a valence of from 1 to 4;

Z is selected from the group consisting of C, Si, Ge, Sn, Pb, N, P, As, Sb, and Bi;

R and R' are selected from the group consisting of hydrogen, halide, $C_1$–$C_{10}$ alkyl and $C_4$–$C_{20}$ aryl;

each X is independently halide;

$X'_2$ is halogen;

X' is halide;

g is an integer from 1 to 13;

h is an integer from 0 to 12;

i is an integer from 0 to 13;

j is an integer from 0 to 5; and k is an integer from 1 to 4;

provided d>h.

Thus, the method of the present invention replaces at least one of the non-fluorine substituent with fluorine.

The compound of the present invention provides a multiple advantages including stability in a variety of thermal or chemical conditions. The compound of the present invention are also weakly coordinating. Thus, the compound of the present invention can be used in a variety of applications including as an activator for catalysts, and as an electrolyte in batteries. These and other advantages will be readily apparent to those skilled in the art, based on the disclosure contained herein.

DETAILED DESCRIPTION OF THE INVENTION

The present invention provides a polyhalogenated monoheteroborane anion of the formula $R_aZB_bH_cF_dX_e(OR'')_f^{-1}$. The term "monoheteroborane" refers to a compound or a moiety in which the core structure contains one non-boron atom attached to boron atoms. The anions of the present invention themselves do not necessarily comprise chemical compounds. Indeed, in an isolable compound, anions must be paired with cations to maintain electroneutrality. Thus, a compound of the present invention is of the formula $M[R_aZB_bH_cF_dX_e(OR'')_f]_k$.

M is a cation having valence of from 1 to 4. M can be any cation including a cation derived from an alkaline metal; alkaline-earth metal; transition metal such as Ag, Zn, Cu, Co, Fe, Mn, Cr, V, Ti, Zr, Rh, Pd, Cd, Hg, Os, Pt, Y, Nb and Mo; lanthanide and actinide series metal; a nitrogen moiety such as ammonium, tetraalkyl ammonium, trialkyl ammonium, dialkyl ammonium, and imminium radical; a phosphorous moiety including tetraalkylphosphonium, and tetraaryl phosphonium. Furthermore, M can be a relatively stable carbocations such as trityl moiety and related carbocations (e.g., $R_3C^+$); and other known cations such as hydronium ($H_3O^+$), $H_5O_2^+$, $(Et_2O)_nH^+$, $H_9O_4^+$, formylium ($HCO^+$), which are known to coordinate with a carborane anion. Preferably, the cation is selected from the group consisting of alkaline metal cations, alkaline-earth metal cations, transition metal cations, ammonium, monohydrocarbyl ammonium, dihydrocarbyl ammonium, trihydrocarbyl ammonium, tetra hydrocarbyl ammonium, tetrahydrocarbyl phosphonium, hydronium, formylium, and trityl and related carbocations; more preferably from the group consisting of trityl and related carbocations, alkaline metal cations, transition metal cations, monohydrocarbyl ammonium, dihydrocarbyl ammonium, trihydrocarbyl ammonium, and tetra hydrocarbyl ammonium; and most preferably from the group consisting of trityl, $Li^+$, $Ag^+$, $Tl^+$, $Cs^+$, $Cu^+$, $Cu^{+2}$, and $Me_2PhNH^+$. As used in this invention, a "hydrocarbyl" refers to compound having at least one carbon atom. Such compounds include aryl, alkyl, alkenyl and alkynyl. Moreover, hydrocarbyl can be straight chain, branched, or cyclic. Hydrocarbyl can also be substituted with other non hydrogen or carbon atoms such as halide, oxygen, sulfur, nitrogen or phosphorus.

M can have one or more ligands (L) including halide such as chloride, bromide and iodide; carbonyl (CO); cyclopentadienyl (Cp) and its derivatives; phosphorous ligand such as trihydrocarbyl phosphine; and other known metal ligands. Preferably a ligand is selected from the group consisting of halides, hydride, carbonyl, cyclopentadienyl and its derivatives, trihydrocarbyl phosphine, hydrocarbyl, nitrosyl, alkoxides, carboxylates, cyanide, cyanate, thiocyanide, thiocyanate and azides; more preferably from the group consisting of carbonyl, halides, hydride, cyclopentadienyl and its derivatives, ammonium, monohydrocarbyl ammonium, dihydrocarbyl ammonium, and trihydrocarbyl ammonium, and trihydrocarbyl phosphonium; and most preferably from the group consisting of carbonyl, halides, cyclopentadienyl and its derivatives, ammonium, monohydrocarbyl ammonium, dihydrocarbyl ammonium, and trihydrocarbyl ammonium.

It will be appreciated that a molar ratio of a cation to a polyhalogenated monoheteroborane anion of the present invention depends on the valence of the cation. This is reflected in the value k, for example, if the cation is monovalent, e.g., cesium or lithium, then k is 1, and there will be a 1:1 molar ratio between the cation and the polyhalogenated heteroborane anion of the present invention. Whereas if the cation is divalent, e.g., calcium or magnesium, then k is 2, and there will be a 1:2 molar ratio between the cation and the polyhalogenated monoheteroborane anion of the present invention. Preferably, k is an integer from 1 to 4, more preferably 1 to 3, still more preferably k is 1 or 2, and most preferably 1.

It should be appreciated that because the polyhalogenated monoheteroborane anion of the present invention is a weakly associating anion, a cation associated with the polyhalogenated monoheteroborane anion can be readily exchanged with another cation by any of the known methods including ion exchange chromatography and other ion exchange methods.

In accordance with the present invention, R is a metal, hydrogen, polymer, halide, $C_1$–$C_{10}$ alkyl, $C_1$–$C_{10}$ alkenyl, $C_1$–$C_{10}$ cycloalkyl, $C_1$–$C_{10}$ alkynyl, or $C_4$–$C_{20}$ aryl. Exemplary metals for R include copper, thallium, lithium, and silver, titanium, zirconium and hafnium. Polymers useful for the present invention are any polymer to which the heteroatom of a polyhalogenated monoheteroborane anion can be attached by a covalent bond. Exemplary polymers useful for the present invention include polyethylene glycol, polyethylene, polypropylene, and polystyrene. As used in this invention, a "polymer" can include a linker which links the polyhalogenated monoheteroborane anion to the polymeric structure.

Alkyl groups according to the invention are aliphatic hydrocarbons which can be straight or branched chain groups. Alkyl groups optionally can be substituted with one or more substituents, such as a halogen, alkenyl, alkynyl, aryl, hydroxy, alkoxy, carboxy, oxo or cycloalkyl. There may be optionally inserted along the alkyl group one or more oxygen, sulfur or substituted or unsubstituted nitrogen atoms. Exemplary alkyl groups include methyl, ethyl, i-propyl, n-butyl, t-butyl, fluoromethyl, difluoromethyl, trifluoromethyl, chloromethyl, trichloromethyl, and pentafluoroethyl. Aryl groups are carbocyclic or heterocyclic aromatic ring moieties. Aryl groups can be substituted with one or more substituents, such as a halogen, alkenyl, alkyl, alkynyl, hydroxy, alkoxy or cycloalkyl. Alkenyl groups are aliphatic hydrocarbons having one or more double bonds between adjacent carbon atoms. Alkenyl groups can be straight or branched chain groups. Exemplary alkenyl groups include vinyl, 1,3-butadienyl, 2-propenyl, chlorovinyl, fluoroethenyl, and tetrafluoroethenyl. Alkynyl groups are aliphatic hydrocarbons having one or more triple bonds between adjacent carbon atoms. Alkynyl groups can further contain a straight or branched chain groups. Exemplary alkynyl groups include ethynyl, 2-propynyl, and 1-propynyl.

In a particularly preferred embodiment, R is preferably hydrogen, halide, $C_1$–$C_{10}$ alkyl or $C_4$–$C_{20}$ aryl; more preferably R is selected from the group consisting of hydrogen, fluoride, methyl, trifluoromethyl, vinyl, ethyl, butyl, fluoromethyl, difluoromethyl and propyl; and most preferably R is selected from the group consisting of hydrogen, fluoride, methyl, trifluoromethyl, ethyl and vinyl.

The possibility of having a various R substitutions will be evident to one of ordinary skill in the art given the guidance and embodiments disclosed in the present specification. For example, the anion $CH_3CB_{11}F_{11}$— is a member of a large class of anions. Organic or inorganic groups can be freely substituted and attached to the carbon atom instead of the $CH_3$ group. Indeed, substitution of an organic group, such as a vinyl, allyl, etc. permits the anion to be incorporated into a polymer having commercially important applications as catalysts, conductors, and materials for the separation of anions and/or molecules. A polyhalogenated monoheteroborane anion such as $HCB_{11}F_{11}^-$ and related anions with a CH bond can readily form a dianion such as $CB_{11}F_{11}^{2-}$ that bind to metal ions through the carbon atom. Such dianions are valuable in that one "equivalent" of anionic charge is coordinating, while the second equivalent of an anionic charge is weakly coordinating. Metal complexes incorporating such design are encompassed by the scope of the present invention. In accordance with the present invention, Z is selected from the group consisting of C, Si, Ge, Sn, Pb, N, P, As, Sb and Bi. Preferably Z is selected from the group consisting of C, Si, N, and P; more preferably from the group consisting of C, N and P; and most preferably Z is C (i.e., a carborane). When Z is a group IV element, such as carbon or silicon, each Z is substituted with a corresponding R group. When Z is a group V element, Z may or may not contain a corresponding R group. It will be appreciated that when Z is a group V element and contains an R group, Z will have a +1 charge and the overall moiety $R_aZB_bH_cF_dX_e(OR")_f$ will be neutral, i.e, it will be a zwitter ion. In such a case, the $R_aZB_bH_cF_dX_e(OR")_f$ moiety can have other corresponding counter ions present near the cation and/or anion sites.

With reference to the formulas described herein:

each X is independently halide. Preferably X is selected from the group consisting of chloride, iodide, and bromide, more preferably X is selected from the group consisting of chloride and bromide, and most preferably X is chloride.

R" is selected from the group consisting of polymer, hydrogen, $C_1$–$C_{10}$ alkyl, $C_1$–$C_{10}$ cycloalkyl, $C_1$–$C_{10}$ alkenyl, $C_1$–$C_{10}$ alkynyl, and $C_4$–$C_{20}$ aryl. Preferably R" is selected from the group consisting of hydrogen, polymer, and $C_1$–$C_{10}$ alkyl. More preferably R" is selected from the group consisting of hydrogen, polymer, $C_1$–$C_{10}$ alkenyl, and $C_1$–$C_{10}$ alkyl.

Preferably, a is 0 or 1.

b is an integer from 5 to 13, preferably b is an integer from 5 to 11. More preferably b is 5, 9 or 11, still more preferably b is 9 or 11, and most preferably b is 11.

c is an integer 0 to 12. Preferably, c is an integer from 0 to 7, more preferably from 0 to 5, and most preferably 0.

d is an integer from 1 to 13, preferably from 2 to 13, more preferably from 2 to 11. Still more preferably d is 5, 9 or 11, yet still more preferably d is 9, or 11, and most preferably d is 11.

e is an integer from 0 to 13. Preferably, e is an integer from 0 to 11, and more preferably from 0 to 5. Most preferably e is 0.

Preferably, f is an integer from 0 to 5, more preferably from 0 to 4, and most preferably from 0 to 3.

It will be appreciated that since each boron atom of the polyhalogenated monoheteroborane anion of the present invention has one substituent, the total number of substituents (i.e., c+d+e+f) is equal to the total number of boron, i.e., c+d+e+f=b.

A compound comprising the polyhalogenated monoheteroborane anion of the present invention can be used in any industrial applications which requires a stable and/or a weakly coordinating anion. For example, the polyhalogenated monoheteroborane anion of the present invention can be used as an activator for catalysts, and as an electrolyte in batteries, for example, lithium salts of the polyhalogenated monoheteroborane monoanions of the present invention can be used as electrolytes for lithium-based batteries useful in such applications as electric vehicles, cell-phones, and laptop computers. Compounds comprising the polyhalogenated monoheteroborane anion are superior co-catalysts (activators) for transition-metal-catalyzed olefin polymerization. There are many other applications as well, ranging from counterions for catalysts for organic reactions to counterions for polymerization and photoinitiators.

The polyhalogenated monoheteroborane anion of the present invention is stable under acidic conditions such as in 20% HCl solution and in 50% $H_2SO_4$ solution. In addition, The polyhalogenated monoheteroborane anion of the present invention is also stable in the presence of a Lewis acid such as $ZnCl_2$, $Et_3Al$, and $SnCl_2$. In fact, the polyhalogenated heteroborane anion of the present invention is slightly acidic when dissolved in water (e.g., $CB_{11}HF_{11}^-$ has pKa of about 13), thus rendering it advantageous for use in a variety of applications known to those of skill in the art. There are many other potential commercial uses of the new anions, for example, as a catalyst in chemical reactions such as a catalyst for Diels-Alder reaction and 1,4-conjugate addition reaction.

Figure 1:
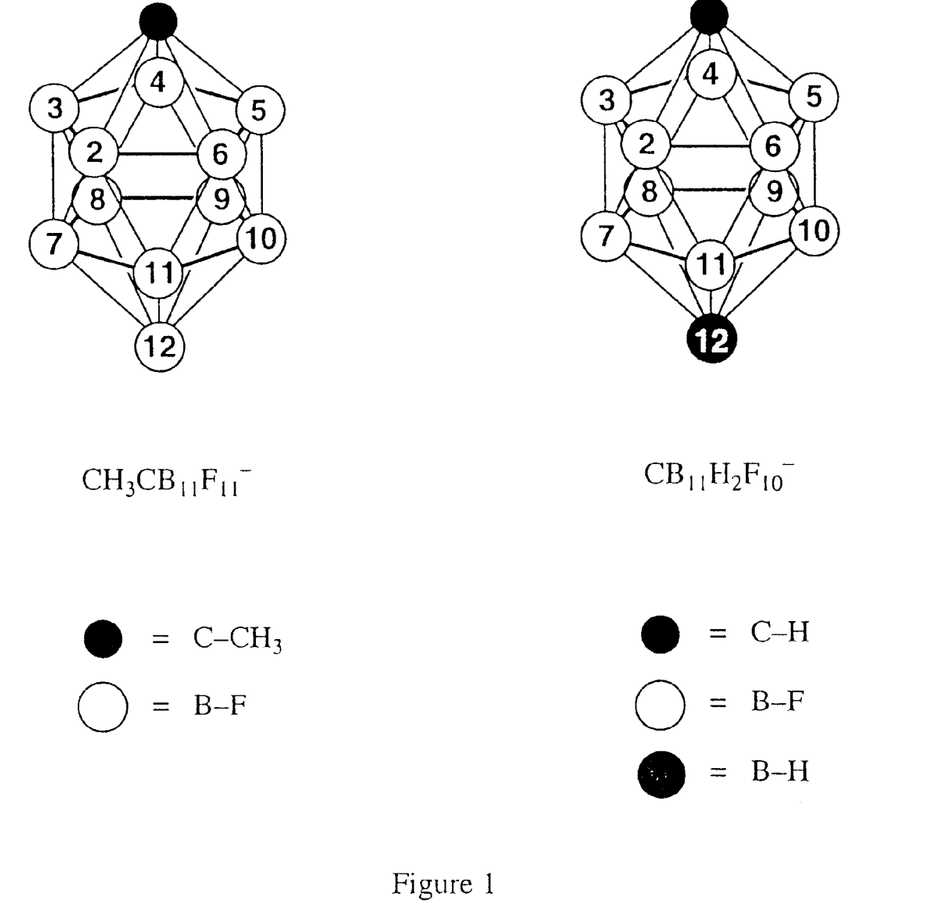
FIG. 1 is a schematic representation of crystal structures of compounds having molecular formulas $CH_3CB_{11}F_{11}^-$ and $HCB_{11}HF_{10}^-$.

In a particularly preferred embodiment of the present invention, the polyhalogenated monoheteroborane anion is a highly fluorinated carborane anion that does not strongly bind or associate with positively charged counter cations (i.e., weakly coordinating anions). Without being bound by any particular theory, the weakly coordinating effect is believed to be due to the presence of a number of fluorine atoms, which decrease the effective anion characteristic through, inter alia, an inductive effect. Two specific examples of anions of the present invention include: 1—$CH_3$-2,3,4,5,6,7,8,9,10,11,12-$CB_{11}F_{11}^-$ ($CH_3CB_{11}F_{11}^-$) and 1,2-$H_2$-3,4,5,6,7,8,9,10,11-$CB_{11}F_{10}^-$ ($HCB_{11}HF_{10}^-$). The possible structures of these anion are depicted in FIG. 1. It is believed that both anions consist of an icosahedron of one carbon and eleven boron atoms; the carbon atom is also believed to be terminally bonded to either a methyl group ($CH_3$) or a hydrogen atom, and each boron atom is believed to be terminally bonded to a fluorine atom or, in the case of B12 in $HCB_{11}HF_{10}$—, a hydrogen atom.

Figure 2:
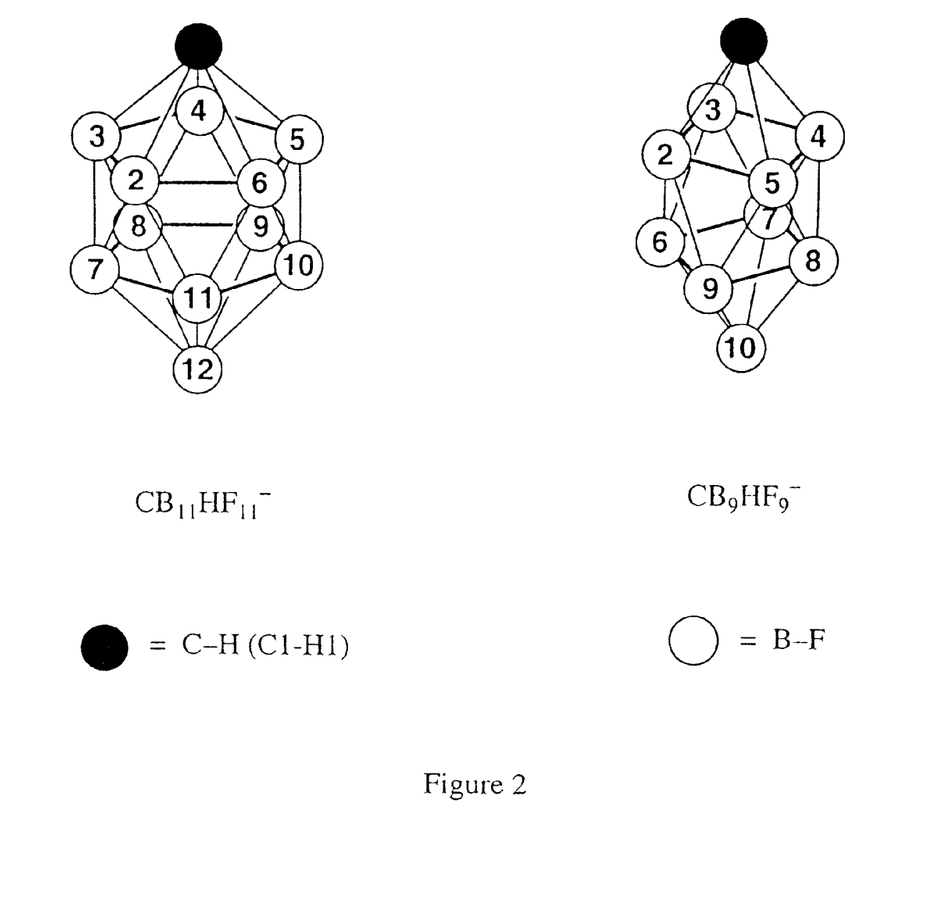
FIG. 2 is a schematic representation of crystal structures of compounds having molecular formulas $HCB_{11}F_{11}^-$ and $HCB_9F_9^-$.

Two other specific examples of anions of the present invention include: 2,3,4,5,6,7,8,9,10,11,12-$HCB_{11}F_{11}^-$ ($HCB_{11}F_{11}^-$) anion and 2,3,4,5,6,7,8,9,10-$HCB_9F_9^-$ ($HCB_9F_9^-$) anion. It is believed that these polyfluorinated monocarborane anions have the structures shown in FIG. 2.

Polyhalogenated heteroborane monoanions of the present invention are weakly coordinating, and as such a compound comprising the polyhalogenated heteroborane anion of the present invention dissociates readily in a variety of solvents. Thus a solution comprising the polyhalogenated monoheteroborane anion of the present invention can readily prepared by dissolving the compound of the present invention in an appropriate solvent. Solvents in which a solution can be prepared include an aqueous solvent; a polar organic solvent and a non-polar organic solvent including hexane, pentane, chloroform, toluene, benzene, xylene, ether, methylene chloride, ethyl acetate, acetonitrile, tetrahydrofuran, alcohols such as methanol and ethanol, glycols, dimethylsulfoxide, dimethyl formamide, dimethoxy ethane, and carbonate solvents such as propylene carbonate and ethylene carbonate; and a combination thereof.

Another advantage of the compounds of the present invention is that they have high solubility in weakly basic solvents. Thus, any reactivity of the cation which is associated with the polyhalogenated monoheteroborane anion of the present invention will be enhanced compared to compounds with other anions.

Polyhalogenated heteroborane monoanions of the present invention can be formulated as a gel by mixing the compound of the present invention with an appropriate polymer using any of the known polymer gel preparation methods. For example, most of the solvent can be removed from a solution comprising a polymer and the compound of the present invention to yield a solvent swollen gel composition comprising the polyhalogenated heteroborane anion of the present invention. Alternatively, a monomer or a precursor of a polymer and the compound of the present invention can be mixed and subjected to a polymerization reaction condition to form a polymer which comprises the polyhalogenated monoheteroborane anion of the present invention. If the resulting polymer is a solid, an appropriate solvent can be added to provide a gelatinous form of the mixture. Polymerization conditions necessary for preparing such a polymer depends on the nature of the monomer or the precursor of the polymer, which are well known to one of ordinary skill in the art of polymerization.

A molten salt comprising the polyhalogenated heteroborane monoanions of the present invention can also be prepared by heating the compound of the present invention until it becomes a liquid. In this manner a molten salt with high electric conductivity can be obtained. Moreover, it will be appreciated that the melting temperature of the compound of the present invention can be lowered by adding impurities. It is well known that a presence of an impurity lowers the melting point of most solids. Thus, a molten salt or a liquid comprising the compound of the present invention at a desired temperature can be prepared by selecting an appropriate impurity and an appropriate amount of the impurity.

Another embodiment of the present invention provides a method for producing polyhalogenated monoheteroborane anion of the present invention (i.e., $R_a ZB_b H_c F_d X_e (OR'')_f^{-1}$) comprising the step of contacting a compound of the formula $M[R'_a ZB_b H_g F_h X_i (OR'')_j]_k$ with a mixture comprising $X'_2$ and HX'. The method of the present invention provides addition of at least one fluorine to the starting material, i.e., d>h. It should be appreciated that the order of adding each component does not have a substantial affect on the composition of the final product. Thus, the method of the present invention includes any and all possible combination of order of addition of each components including a method where HX' is added to the compound of the formula $M[R'_a ZB_b H_g F_h X_i (OR'')_j]_k$ prior to $X'_2$, a method wherein $X'_2$ is added to the compound of the formula $M[R'_a ZB_b H_g F_h X_i (OR'')_j]_k$ prior to HX', and a method where $X'_2$ and HX' are added simultaneously to the compound of the formula $M[R'_a ZB_b H_g F_h X_i (OR'')_j]_k$.

R' is hydrogen, polymer, $C_1$–$C_{10}$ alkenyl, $C_1$–$C_{10}$ alkynyl, $C_1$–$C_{10}$ cycloalkyl, $C_4$–$C_{20}$ aryl, halide, or $C_1$–$C_{10}$ alkyl. Preferably R' is hydrogen, halide or $C_1$–$C_{10}$ alkyl, more preferably R' is hydrogen or $C_1$–$C_{10}$ alkyl.

$X'_2$ is halogen. Preferably $X'_2$ is fluorine.

X' is halide. Preferably X' is fluoride.

g is an integer from 1 to 13, preferably from 4 to 13, more preferably from 4 to 11. Still more preferably g is 4, 5, 8, 9, 10, or 11, and most preferably g is 8, 9, 10 or 11. Alternatively g is at least b−4, more preferably at least b−2 and most preferably b.

h is an integer from 0 to 12, more preferably h is less than about 3, and most preferably h is 0 or 1.

Preferably i is an integer from 0 to 13, more preferably from 0 to 11. Still more preferably i is 0, 1, 9 or 11, and most preferably 0.

j is an integer from 0 to 5, preferably from 0 to 4, more preferably from 0 to 2. Most preferably j is 0.

The present method can include a step of drying the compound of the formula $M[R'_a ZB_b H_g F_h X_i(OR'')_j]_k$ or the reaction vessel using a heat or a desiccant. The drying can be conducted under an atmospheric pressure of an inert gas, such as nitrogen, argon or helium, or it can be conducted under vacuum.

The method of the present invention generally involves cooling the reaction vessel containing a compound of the formula $M[R'_a ZB_b H_g F_h X_i(OR'')_j]_k$ to a temperature sufficient to allow condensation of HX'. Typically, the reaction vessel is cooled to about −78° C. Preferably from about 10 equivalents (equiv.) of HX' to about 1000 equiv. of HX' is added to the reaction vessel, more preferably from about 200 equiv. to about 700 equiv., and most preferably from about 300 equiv. to about 500 equiv. Although it is not necessary, HX' can be dried by passing it through a drying agent, such as molecular sieves, prior to condensation.

The Method of the present method also includes adding halogen (X'$_2$) to the reaction vessel. Although not necessary, halogen can be dried prior to being added to the reaction vessel. Halogen can be added in a pure form or it can be added as a dilute gaseous solution. A dilute gaseous solution of halogen can be formed by mixing the halogen with an inert carrier gas such as nitrogen, helium or argon. Preferably the carrier gas is nitrogen. For a small scale reaction, it is preferred that the halogen be added as a dilute gaseous solution. This allows better control of the amount of halogen that is added to the reaction vessel. Addition of a halogen typically involves cooling the reaction vessel to about −78° C. and condensing the desired amount of the halogen into the reaction vessel. Preferably from about 5 equiv. of halogen to about 20 equiv. of halogen is added to the reaction vessel, more preferably from about 10 equiv. to about 16 equiv., and most preferably from about 13 equiv. to about 15 equiv.

After the addition of necessary reactants, the reaction vessel is typically sealed to provide a closed system, and the reaction mixture is mixed by any appropriate method of providing agitation of the reaction mixture, for example, rotating or shaking the reaction vessel, or stirring the reaction mixture. Typically the reaction mixture is brought back to room temperature and the reaction vessel is rotated (i.e., spun) or shaken to provide a sufficient mixing of the reactants to allow a desired reaction to occur. It will be appreciated that when the reaction mixture is brought to room temperature, the pressure inside the reaction vessel will increase significantly due to re-vaporization of halogen and/or HX. Therefore, the reaction vessel should be carefully selected to be able to withstand this increase in pressure. Preferably the reaction time is from about 1 h to about 72 h, more preferably from about 5 h to about 48 h, and most preferably from about 8 h to about 24 h. The final reaction temperature is less than about 100° C., and more preferably less than about 50° C. Most preferably the final reaction temperature is at about room temperature.

A compound comprising the polyhalogenated monoheteroborane anion of the present invention can be isolated by removing any remaining gaseous reactant, e.g., HX', and/or halogen (X'$_2$).

When R' is hydrogen or a moiety containing a hydrogen such as alkyl or aryl, some or all of the hydrogens present in R' can also be replaced by X' in the course of reaction.

Another embodiment of the present invention provides a polyhalogenated monoheteroborane anion produced by the process of the above described methods.

EXAMPLES

Example 1

This example illustrates a method for producing a cesium salt of monocarborane polyhydride.

To 400 mg of $[(CH_3)_3NH]CB_9H_{10}$ in 40 mL of water was added 89 mg of sodium hydroxide. The resulting solution was stirred under water aspirator generated vacuum to remove $(CH_3)_3N$ gas. The resulting clear solution was acidified to pH of about 2 and a solid precipitate which formed was removed by a filtration. About 0.5 g of CsCl was added to the filtrate and the resulting solid precipitate was filtered and dried to yield $CsCB_9H_{10}$ as a white solid.

Example 2

This example illustrates a method for producing polyfluorinated monocarborane anion from monocarborane hydride.

About 35 mg of $CsCB_{11}H_{12}$ was placed in a monel reactor and was heated under vacuum to about 80° C. to 100° C. for about 0.5 h. The reactor was cooled and about 20 mL of HF was condensed into the reactor at about −70° C. About 30 pounds per square inch (psi) of 10% $F_2$ in $N_2$ was also condensed into the reactor at −70° C. The reactor was allowed to warm to room temperature and the reactor was rotated. After about 3 days, the reaction mixture was cooled to −70° C. and the gases were removed via vacuum. About 1.5 mL of deuterated acetone was added and the resulting solution was filtered. $^{11}B$ NMR and $^{19}F$ showed presence of mostly $CB_{11}F_{11}H^-$.

The reactor was washed with an additional 3 mL of acetone. Both of the acetone solutions were combined and concentrated to yield a brown oil. The oil was dissolved in about 15 mL of water. The aqueous solution was neutralized by adding CsOH. A brown solid precipitated and was removed by filtration. Water was removed from the filtrate to provide a white solid. The white solid was dissolved in acetone and filtered. Removal of acetone from the filtrate provided 27 mg (47% yield) of $CsCB_{11}F_{11}H$ as a white solid. $^1H$ NMR $[(CD_3)_2CO, \delta]$: 3.98. $^{11}B$ NMR: −7.8, −15.9 and −17.4. $^{19}F$ NMR: −251.3, −255.0, and −255.7.

Example 3

This example illustrates the effect of the absence of hydrogen fluoride on the product formation.

The same procedure as set forth in Example 2 was used except that no HF was added to the reaction mixture. $^{11}B$ NMR showed only a very small amount of $HCB_{11}F_{11}^-$ had formed.

Example 4

This example illustrates the effect of the absence of fluorine gas on the product formation.

The same procedure as set forth in Example 2 was used except that no $F_2$ was added to the reaction mixture. About 15 mg (25% yield) of $HCB_{11}F_{11}^-$ was obtained as a slightly pink solid.

Example 5

This example illustrates the effect of fluorination on carborane polyhydrides having a methyl substituent.

The same procedure as set forth in Example 2 was used except that 37 mg of Cs (1-CH$_3$CB$_{11}$H$_{11}$) was used instead of CsCB$_{11}$H$_{12}$. Analysis of a crude product showed that the following three compounds in the ratio of about 1:4.5:1.2, respectively, was obtained.

1-CH$_3$—CB$_{11}$F$_{11}$$^{31}$.
$^1$H NMR [(CD$_3$)$_2$CO, δ]: 1.53. $^{11}$B NMR: −6.9 and −16.1.
1-CH$_2$F—CB$_{11}$F$_{11}$$^-$.
$^1$H NMR [(CD$_3$)$_2$CO, δ]: 5.21 (J=46 Hz). $^{19}$F NMR: −228.8 (J=46 Hz). $^{11}$B NMR: −6.9 and −16.1.
1-CHF$_2$—CB$_{11}$F$_{11}$$^-$.
$^1$H NMR [(CD$_3$)$_2$CO, δ]: 6.76 (J=52 Hz). $^{19}$F NMR: −109.4 (J=52 Hz). $^{11}$B NMR: −6.9 and −16.1.

In addition, a very small amount of HCB$_{11}$F$_{11}$$^-$ appeared to be present in the mixture.

Purification via recrystallization resulted in the disappearance of 1-CHF$_2$—CB$_{11}$F$_{11}$$^-$.

Example 6

This example illustrates a synthesis of CB$_9$HF$_9$$^-$.

The same procedure as set forth in Example 2 was used except that CsCB$_9$H$_{10}$ was used instead of CsCB$_{11}$H$_{12}$. A mixture of CB$_9$HF$_9$$^-$ and (CB$_9$HF$_8$)$_2$$^{-2}$ was obtained.

The reaction was worked-up using the same procedure as set forth in Example 2 except that Bu$_4$NF was added to the water solution to precipitate out slightly yellow Bu$_4$N$^+$ salts, as follows:

HCB$_9$F$_9$$^-$ salt:
$^{11}$B NMR [(CD$_3$)$_2$CO, δ]: 9.1, −4.9 and −5.6. $^{19}$F NMR: −225.8, −226.3 and −230.1.
(HCB$_9$F$_8$)$_2$$^{-2}$ salt:
$^{11}$B NMR [(CD$_3$)$_2$CO, δ]: −1.7 and −6.2. $^{19}$F NMR: −215 and −222.

Example 7

This example provides a comparison of a product formation using CsHCB$_{11}$H$_{11}$ and CsHCB$_{11}$H$_{10}$F as a starting material.

The same procedure as set forth in Example 2 was used in a side-by-side comparison reaction using CsHCB$_{11}$H$_{11}$ and CsHCB$_{11}$H$_{10}$F (containing about 10% to 15% CsHCB$_{11}$H$_{11}$) as starting materials in a separate monel reactors.

An analysis of the crude products showed that the CsHCB$_{11}$H$_{10}$F reaction has a much smaller amount of unreacted starting material.

Both reactions were worked-up using the same procedure as set forth in Example 2 except that Bu$_4$NF was added to the water solution to precipitate out (Bu$_4$N)HCB$_{11}$F$_{11}$ salts.

CsHCB$_{11}$H$_{11}$ reaction provided 76% yield of (Bu$_4$N)HCB$_{11}$F$_{11}$. And CsHCB$_{11}$H$_{10}$F reaction gave 72% yield of (Bu$_4$N)HCB$_{11}$F$_{11}$.

Example 8

This example provides the identity of other isomers formed in a fluorination reaction using CsHCB$_{11}$H$_{10}$F as a starting material.

The same procedure as set forth in Example 2 was used except that 220 mg of CsHCB$_{11}$H$_{11}$F (containing about 10% to 15% CsHCB$_{11}$H$_{11}$) was used instead of CsHCB$_{11}$H$_{11}$. $^{19}$F NMR analysis of the crude product showed the relative amount of HCB$_{11}$F$_{11}$$^-$ compared to other isomers was >95%. Other identified isomers in the crude product include 7,12-HCB$_{11}$H$_9$F$_2$$^-$, HCB$_{11}$HF$_{10}$$^-$, and HCB$_{11}$H$_2$F$_9$$^-$.

Purification using the method of Example 2 provided 205 mg (58% yield) of CsHCB$_{11}$H$_{11}$ as a solid. $^{13}$C NMR [(CD$_3$)$_2$CO, δ]: 15.8 (J=172 Hz).

Example 9

This example illustrates the stability of CsHCB$_{11}$F$_{11}$ in an acidic condition.

To about 19.8 mg of CsHCB$_{11}$F$_{11}$ was added about 1 mL of a solution containing 20% DCl in D$_2$O. The solution was monitored for two weeks by NMR. A solution of about 40 mg of Ph$_4$PCl in 3 mL of water was added. The resulting precipitate was filtered and dried to provide 26 mg (92% recovery) of (Ph$_4$P)HCB$_{11}$F$_{11}$ as a white solid.

Example 10

This example provides a method for substituting one or more fluorides in CsHCB$_{11}$F$_{11}$ with hydroxides.

To about 19.8 mg of CsHCB$_{11}$F$_{11}$ was added about 1 mL of 3 M KOH solution. The solution was monitored for two weeks by NMR. A solution of about 55 mg of Ph$_4$PCl in 5 mL of water was added. The resulting precipitate was filtered to provide about 3 mg of a white solid comprising mostly of HCB$_{11}$H$_{10}$F$^-$ and HCB$_{11}$H$_9$F(OH)$^-$ with a small amount of HCB$_{11}$F$_{11}$$^-$. The filtrate was acidified to pH of about 1 with HCl, and the resulting precipitate was filtered and dried to provide 18 mg of HCB$_{11}$F$_9$(OH)$_2$$^-$ salt as a white solid. IR (cm$^{-1}$): 3619, 3604. NIEMS (m/z): 337.3. $^{11}$B NMR [(CD$_3$)$_2$CO, δ]: −9.4, −18.2, and −20.5. $^{19}$F NMR: −249.7, −252.8, −254,1, −254.8, and −256.3.

Example 11

This example illustrates a method for substituting one or more fluorides in CsHCB$_{11}$F$_{11}$ with hydrides.

To a reaction flask about 0.8 g of Na was added to a solution of 38.6 mg of CsHCB$_{11}$F$_{11}$ in 8 mL of THF. After 20 h, the THF solution was transferred to a 50-mL Schlenk flask via a cannula. The reaction flask was rinsed with 15 mL of THF. The THF solutions were combined and concentrated to provide a solid. The solid was dissolved in about 2 mL of D$_2$O, and a solution of 30,5 mg Ph$_4$PCl in 1 mL of D$_2$O was added. The resulting white solid precipitate was filtered and dried to provide 35 mg of Ph$_4$P salt of HCB$_{11}$HF$_{10}$$^-$ as a white solid. $^{11}$B NMR: −13.8, −15.9 and −29.8 ($J_{B-H}$=138 Hz).

Example 12

This example illustrates a method for separating CsHCB$_{11}$F$_{11}$ from CsHCB$_{11}$H$_{10}$F.

To 180 mg of about 1:1 mixture of CsHCB$_{11}$F$_{11}$ and CsHCB$_{11}$H$_{10}$F was added about 0.5 g of AgNO$_3$. After about 2 h, the solid turned brown. About 30 mL of benzene was added via a cannula and the mixture was stirred for about 20 h. Dark solid was removed by a filtration and washed with acetone to provide a substantially pure HCB$_{11}$F$_{11}$$^-$ salt.

The benzene filtrate was concentrated and dried to provide a brown solid. The brown solid was treated with 2 mL of CH$_2$Cl$_2$, stirred for 5 min. and filtered. Dissolving the filtered solid in acetone and analyzing it with NMR analysis showed a presence of HCB$_{11}$H$_{10}$F$^-$ and HCB$_{11}$F$_{11}$$^-$ salts in the ratio of about 2:1. The CH$_2$Cl$_2$ filtrate showed a presence of HCB$_{11}$F$_{11}$$^-$ and FCB$_{11}$H$_{11}$$^-$ salts in the ratio of about 3:1.

Ag ($C_6H_6$) $HCB_{11}H_{10}F$.
$^{11}B$ NMR [$(CD_3)_2CO$, δ]: 14.8, −14.2 and −18.2. $^{19}F$ NMR: −190.0.
Ag ($C_6H_6$) $HCB_{11}F_{11}$.
$^{11}B$ NMR [$(CD_3)_2CO$, δ]: −7.8, −15.7 and −17.2. $^{19}F$ NMR: −251.2 and −255.1.

Example 13

This example illustrates the stability of $CsHCB11F11$ in hot water.

To about 145 mg of $CsHCB_{11}F_{11}$ was added about 1.5 mL of water, and the resulting solution was heated to about 80° C. The solution was cooled to room temperature and the solid was separated. The liquid layer showed presence of $CsHCB_{11}F_{11}$ and $CsHCB_{11}F_{10}(OH)$.

Example 14

This example provides a method for preparing $HCB_{11}F_{11}^-$ having trimethyl ammonium counter cation.

Same procedure as Example 2 was used except 250 mg of $CsHCB_{11}H_{11}$ was used instead. The reactor was rotated (i.e., spun) for 64 h. The aqueous work-up was also modified to include $Me_3NHCl$ salt. The solid precipitate was dried under vacuum for 1 day to provide 258 mg (71% yield) of $(Me_3NH)HCB_{11}F_{11}$ as a white solid.

Example 15

This example provides a method for replacing the hydrogen atom attached to the carbon atom with a fluorine atom.

To a solution of about 211 mg of N-fluoro-N'-chloromethyl 1,8-diazabicyclo[2,2,2]octane bis (tetrafluoroborate) ("F-TEDA") in about 2 mL of water was added a solution of 23 mg of $CsH^{13}CB_{11}F_{11}$ in about 1.5 mL of water. The mixture was stirred at room temperature for 20 h. The white solid precipitate was removed by a filtration. A solution of sodium hydroxide was added to the filtrate to adjust the pH to about 12, and the resulting mixture was stirred for about 0.5 h. The solution was neutralized with HCl and $Bu_4NCl$ salt was added. The slightly yellow solid precipitate contained $FCB_{11}F_{11}^-$ salt.

Example 16

This example illustrates a method for alkylating the carbon atom of a polyhalogenated monocarborane anion salt.

To a 100 mL round-bottomed flask was added about 0.55 g of $CsHCB_{11}F_{11}$ followed by about 30 mL of 2.5% NaOH solution. $Me_3N$ was removed from the solution via a rotary evaporator for about 10 to 15 min. The resulting solution was transferred to 50 mL Erlenmeyer flask and diluted to about 40 mL with water, and about 1 mL of dimethyl sulfate was added to the solution and stirred for about 1 h. The solution was acidified to pH of about 1 with 1 M HCl solution, and the solution was filtered. The filtrate was extracted with ether (3×50 mL). The organic layer was concentrated and the resulting residue was diluted with about 20 mL of water, and $Me_3NHCl$ was added. The resulting solid precipitate was filtered and dried to provide 0.468 g (82% yield) of $(Me_3NH)CH_3CB_{11}F_{11}$. The filtrate can be further precipitated to provide about 10 mg (5% yield) of $(Me_3NH)CH_3CB_{11}F_{11}$. $^{11}B$ NMR (δ): −8.4, −16.3 and −17.2. $^{19}F$ NMR: −250.2, −255.4, and −256.8. $^1H$ NMR: 1.51.

Alternatively, cesium salt can be prepared as follows:

To a 50 mL round bottomed flask was added about 200 mg of $(Me_3NH)HCB_{11}F_{11}$ followed by about 10 mL of 5% NaOH solution. $Me_3N$ was removed from the solution via a rotary evaporator for about 10 min. The reaction mixture was filtered and the filtrate was dilute to 30 mL with water. About 0.45 mL of dimethyl sulfate was added to the aqueous solution and stirred for about 0.5 h. The aqueous solution was acidified to pH of about 1 to 2 with 1 M HCl solution. The aqueous layer was extracted with ether (3×50 mL). The organic layer was concentrated and the resulting residue was diluted with about 5 mL of water, and about 1 mL of CsCl (about 0.25 g) solution was added. The mixture was cooled to about 4° C. and filtered. The solid precipitate was washed twice with about 4 mL of ca. 0° C. water. The solid was dried under vacuum and recrystallized from acetone and water to provide 165 mg (68% yield) of $CsCH_3CB_{11}F_{11}$. The filtrate can be further precipitated to provide about 10 mg (5% yield) of $(Me_3NH) CH_3CB_{11}F_{11}$.

Example 17

This example illustrates a method for substituting one or more fluorides in $CsCH_3CB_{11}F_{11}$ with hydrides.

A solution of 17 mg of $CsCH_3CB_{11}F_{11}$ in 5 mL of THF was added to a Young tube containing 0.2 g of Na. The mixture was stirred for 25 h. The solution was then transferred via a cannula to a Schlenk flask and concentrated. The resulting white solid precipitate showed 41% conversion of $CsCH_3CB_{11}F_{11}$ to $CsCH_3CB_{11}HF_{10}$. $^{19}F$ NMR: −244.0 and −252.9. $^{11}B$ NMR: −14.0, −15.8 and −29.6 ($J_{B-H}$=138 Hz).

Example 18

This example illustrates a method for synthesizing other isomers of polyfluorinated monocarborane anion salts.

A mixture of about 100 mg of $CsH^{13}CB_{11}H_{11}$ and about 10 mL of HF in a bomb apparatus was heated at about 370° C. for about 90 h. The reaction mixture was cooled and unreacted HF was removed. The resulting residue was transferred to a round bottom flask using about 10 mL of acetone. The resulting solution was concentrated and the residue was diluted with about 20 mL of water and neutralized with CsOH. The aqueous mixture was concentrated and the residue diluted with about 5 mL of acetone and filtered. The filtrate was concentrated to provide a mixture of compounds comprising $CsHCB_{11}H_{11-x}F_x$, where x is an integer from 6 to 9. The relative ratio of isomers was 6:14:4:1 for x=6, x=7, x=8 and x=9, respectively.

Example 19

This example illustrates a method for making a polyhalogenated heteroborane anion salt having a trityl counter cation.

A solution of about 300 mg of $AgCH_3CB_{11}F_{11}$ and about 182 mg of $Ph_3CCl$ in about 30 mL of $CH_2Cl_2$ was stirred for 1 h. A white precipitate of AgCl was removed by a filtration, and the filtrate was concentrated and dried under vacuum for about 20 h to provide $Ph_3C(CH_3)CB_{11}F_{11}$ and $Ph_3CCl$ mixture. $Ph_3CCl$ was removed by washing the mixture with isooctane to provide about 190 mg of $Ph_3C(CH_3)CB_{11}F_{11}$. $^1H$ NMR for —CH3 group in $CD_2Cl_2$:
  $AgCH_3CB_{11}F_{11}$: δ=1.545
  $Ph_3C(CH_3)CB_{11}F_{11}$: δ=1.49

Example 20

This example illustrates a method for preparing a lithium salt of a polyhalogenated heteroborane anion salt.

A solution of 9.3 mg of $Li_2CO_3$ in 30 mL of water is added to 100 mg of $(Me_3NH)CH_3CB_{11}F_{11}$. The solution was concentrated in a rotary evaporator. Additional 30 mL of water was added, and the resulting solution was again concentrated in a rotary evaporator. About 30 mL of water and 2 mg of $Li_2CO_3$ was added, and the resulting solution was once again concentrated in a rotary evaporator. Drying the resulting residue provided 78 mg of hydrated $LiCH_3CB_{11}F_{11}$ as a white solid.

Example 21

This example illustrates that dry $LiCH_3CB_{11}F_{11}^-$ salt can be obtained by heating $(H_2O)_n LiCH_3CB_{11}F_{11}^-$ salt.

DSC was done on 9.9 mg of the solid obtained in Example 20.

Run #1: last endoeffect at 170° C.
Run #2: last endoeffect at 155° C.
Run #3: last endoeffect at 146° C.

Example 22

This example illustrates a preparation of Proton-Sponge® salt of a polyhalogenated heteroborane anion.

To a 100 mL round-bottomed flask was added about 100 mg of $(Me3NH)HCB11F11$ followed by a solution of 20 mg of $Li2CO3$ in 40 mL of water. The resulting solution was concentrated via a rotary evaporator. The resulting solid residue was dissolved in 30 mL of water and about 2 mL of 1 M HCl was added. The resulting aqueous layer was extracted twice with 50 mL portions of ether. The organic layers were combined, concentrated to about 5 mL of volume, transferred to a 25 mL Schlenk flask, and dried under vacuum for 0.5 h to provide a pink-red oil. To this oil was added a solution of about 101.2 mg of Proton-Sponge® in 1 mL of $CD2Cl2$ was added. After 20 min., $CD2Cl2$ was removed under vacuum. The resulting yellow solid was further dried under vacuum, washed with 20 mL of hexane and once again dried under vacuum to provide 96 mg of $[C_{10}H_6(NMe_2)_2H]^+HCB_{11}F_{11}^+$ as a yellowish solid.

Example 23

This example illustrates a method for converting $Me_3NH^+$ counter cation to $Cs^+$ counter cation of a polyhalogenated heteroborane anion salt.

To a 50 mL round-bottomed flask is added about 368 mg of $(Me_3NH)CH_3CB_{11}F_{11}$ and a solution of 60 mg of NaOH in 15 mL of water. $Me_3N$ was removed under vacuum and the solution was neutralized with 1 M HCl. To the resulting mixture was added a solution of 250 mg of CsCl, and the solid precipitate was filtered and dried to provide 392 mg (90% yield) of $CsCH_3CB_{11}F_{11}$ as a white solid.

Example 24

This example illustrates a method for converting $Cs^+$ counter cation to $Ag^+$ counter cation of a polyhalogenated heteroborane anion salt.

A solution of about 425 mg of $CsCH_3CB_{11}F_{11}$ and 1.2 g of $AgNO_3$ in about 150 mL of benzene was stirred at about 70° C. for about 24 h. The solution was cooled to room temperature and filtered. The filtrate was concentrated and dried under vacuum to provide a white solid. The white solid was dissolved in about 20 mL of methylene chloride, stirred for about 15 min., and filtered. The methylene chloride filtrate was concentrated and dried to provide about 410 mg (87% yield) of $AgCH_3CB_{11}F_{11} \cdot C_6H_6$ as a yellowish-white solid.

$(C_6H_6)AgCH_3CB_{11}F_{11}$ has solubility of about 0.2 g/mL in $CH_2Cl_2$ and about 1 to 2 mg/mL in benzene. $(C_6H_6)AgCH_3CB_{11}F_{11}$.

$^1H$ NMR ($CD_2Cl_2$, δ): 1.58. $^{19}F$ NMR: −253.5, −257.7, and −259.5. $^{11}B$ NMR: −11.8 and −20.2.

Example 25

This example illustrates a method for making a dilithium salt of a polyhalogenated heteroborane dianion.

To a solution of about 0.2 g of $(Me_3NH)HCB_{11}F_{11}$ in about 25 mL of THF at 0° C. was added about 0.33 mL of 0.3 M nBuLi solution in hexane. The resulting reaction mixture was stirred at room temperature for about 1 h, concentrated, and dried under vacuum to provide about 180 mg of $Li_2CB_{11}F_{11} \cdot THF$ as a slightly yellowish-white solid. $Li_2CB_{11}F_{11}$.

$^{19}F$ NMR ($CD_3CN$, δ): −231.0, −235.6 and −271.2.

Example 26

This example illustrates a method of fluorinating a dilithium salt of a polyhalogenated heteroborane dianion.

To a suspension of about 25 mg of F-TEDA in about 0.6 mL of $CH_3CN$ was added a solution of about 20 mg of $Li_2CB_{11}F_{11}$ in 1 mL of $CD_3CN$ and stirred at room temperature. $^{19}F$ NMR showed formation of $LiFCB_{11}F_{11}$. $^{19}F$ NMR (δ): −243.3, −248.7, −255.8, and −265.0. NIEMS (m/z): 359.2.

Example 27

About 50 mL of 0.5 M NaOH solution was added to about 0.60 g of $[(CH_3)_3NH]HCB_{11}F_{11}$. About 10 mL of water was removed under vacuum. About 0.5 mL of diethylsulfate was added to the resulting solution and stirred at room temperature for about 40 min. About 3 mL of ethanol was added to the solution and stirred for additional 1 h. The solution was acidified with HCl to pH of about 3 and concentrated to a volume of about 20 mL. The resulting solution was treated with about 0.34 g of CsCl in water whereupon a white solid precipitated. The solid was filtered, washed with 2 mL of cold water and dried under vacuum to provide 0.51 g (67%) of $Cs(CH_3CH_2CB_{11}F_{11})$. $^{19}F$ NMR (acetone-$d_6$, δ): −249.4, −253.7 and −256.6. $^1H$ NMR: 1.23 (3H) and 2.33 (2H).

Example 28

Procedure of Experiment 24 was used to prepare $(C_6H_6)AgEtCB_{11}F_{11}$ in 84% yield. (Et=$CH_3CH_2$).

Example 29

To 10 mg of fluorolube mull of $(C_6H_6)AgEtCB_{11}F_{11}$ was added about 952 torr of CO. IR spectra showed formation of $(C_6H_6)(CO)AgEtCB_{11}F_{11}$ (λ=2199 $cm^{-1}$). When the sample was placed under vacuum for 48 h, CO was removed with the formation of starting material $(C_6H_6)AgEtCB_{11}F_{11}$.

Example 30

To a solution of 0.46 g of $(Me_3NH)HCB_{11}F_{11}$ in 30 mL of THF was added 0.92 mL of 2.5 M solution of n-BuLi in hexane solution. The resulting mixture was stirred for 3 h and placed under vacuum for 1 min to remove trimethylamine. The solution was then treated with 0.25 mL of nBuBr and stirred for 18 h. THF was removed under vacuum and 15 mL of water was added. The resulting solution was filtered to remove solids. A solution of 0.34 g of CsCl in water was added to the filtrate. The white precipitate was collected by filtration, washed with 2 mL of cold water and dried under vacuum to yield 0.40 g (65%) of Cs(1-n-BuCB$_{11}$F$_{11}$). $^{19}$F NMR (acetone-d6, δ): −249.3, −253.2, and −256.6. $^1$H NMR: 0.92 (3H), 1.35 (2H), 1.69 (2H), 2.17 (2H).

Example 31

A solution of n-BuLi (0.33 mL, 3.0 M) in hexane was added to a solution of 0.20 g of (Me$_3$NH)1-H-CB$_{11}$F$_{11}$ in 30 mL of THF and stirred for 1 h and then placed under vacuum and dried for 24 h to yield 180 mg of [(THF)$_n$Li]$_2$CB$_{11}$F$_{11}$.

Example 32

The solution of 26 mg of [(THF)$_n$Li]$_2$CB$_{11}$F$_{11}$ in 1 mL of CH$_3$CN was treated with a suspension of 25 mg of F-TEDA in 0.6 mL of acetonitrile. $^{19}$F NMR and NIEMS showed mixture of CB$_{11}$F$_{12}$$^-$ and HCB$_{11}$F$_{11}$$^-$. Acetonitrile was removed under vacuum and addition of 15 mL of water resulted in formation of 24 mg of (H-TEDA) (FCB$_{11}$F$_{11}$)$_2$ as a yellowish solid.

Example 33

A solution of 39 mg of CsHCB$_{11}$F$_{11}$ in 10 mL of THF was treated with 1 g of Na for 20 h under Ar atmosphere. THF was removed using canula to 25 mL Schlenk flask and other volatile compounds were removed under vacuum. The remaining solid was dissolved in water and treated with an aqueous solution of Ph$_4$PCl. The white precipitate was filtered, washed with 5 mL of water and dried under vacuum to yield 35 mg (65%) of (Ph$_4$P) (1,12-CB$_{11}$H$_2$F$_{10}$).

Example 34

About 0.10 g of Cs(1-Me-CB$_{11}$F$_{11}$) was dissolved in 50 mL of 0.1 M HCl solution. The solution was extracted with two 50 mL portions of ether. The organic layers were combined, concentrated, and dried to yield 52 mg (65%) of (H$_5$O$_2$) (1-Me—CB$_{11}$F$_{11}$) as a red solid.

Example 35

A mixture of 0.18 g of Cs(1-Et—CB$_{11}$F$_{11}$) and 0.9 g of (PhN(Me)$_2$H)Cl in 10 mL of acetone was stirred for 1 h. The solid was removed by a filtration. The filtrate was concentrated and the resulting white solid was recrystallized from 5 mL of CD$_2$Cl$_2$ to yield colorless solid. $^1$H NMR (acetone-d6, δ): 2.91 [PhN(Me)$_2$], 3.20 [(PhN(Me)$_2$H)Cl], 3.43 [(PhN(Me)$_2$H) (1-Et—CB$_{11}$F$_{11}$].

Example 36

A solution of 0.10 g of Cs(1-Me—CB$_{11}$F$_{11}$) in 50 mL of 0.1 M HCl solution was extracted with two 100 mL portions of ether. The organic layers were combined, concentrated and dried to yield 52 mg of a pink solid. $^1$H NMR in CD$_3$CN showed presence of at least 6 protons (δ: 9.11) per carborane cluster. When about 3 mg of this solid was dissolved in 1 mL of water, the pH of resulting solution was about 1. This indicated that the solid is a strong acid, which has a composition (H$_7$O$_3$) (1-Me—CB$_{11}$F$_{11}$) or the mixture of (H$_5$O$_2$) (1-Me—CB$_{11}$F$_{11}$) and (H$_7$O$_3$) (1-Me—CB$_{11}$F$_{11}$) and may be (H$_9$O$_4$) (1-Me—CB$_{11}$F$_{11}$). This compound was heated at 160° C. for 3 days under vacuum. $^1$H NMR of dried solid showed presence of 4 protons (δ: 10.30) per carborane cluster and a broad signal (δ: 8.8) with relative intensity of about 0.9, which indicates the solid is (H$_5$O$_2$) (1-Me—CB$_{11}$F$_{11}$).

When 1700 psi of CO was added to a fluorolube mull of (H$_5$O$_2$) (1-Me—CB$_{11}$F$_{11}$) in high pressure IR cell, a signal at λ=2183 cm$^{-1}$ was observed. This stretching frequency corresponds to HCO$^+$ specie which indicates the presence of (HCO) (1-Me—CB$_{11}$F$_{11}$).

Example 37

About 10 mg of (PhAg) (1-Bu—CB$_{11}$F$_{11}$) was heated at 135° C. in 10% H$_2$/N$_2$ mixture. The color of the solid changed from white to brown. The solid was dissolved in 1 mL of CD$_2$Cl$_2$ and black solid was filtered. $^1$H and $^{19}$F NMR showed no anion decomposition. Analysis of brown solid showed presence of Ag in the solid. When the solution of very weak base (about 3 mg of Ph$_3$N, pKa~5) was added to the solid, a brown solution formed. Broad signal for aromatic protons of Ph$_3$N was observed by $^1$H NMR. CD$_2$Cl$_2$ was removed, and the white solid was washed with hexane and redissolved in benzene-d6. $^1$H NMR showed acidic proton with δ at 10.6. Benzene was removed and the solid was redissolved in acetonitrile-d3. $^1$H NMR showed (Ph$_3$NH) (1-Bu—CB$_{11}$F$_{11}$). $^1$H NMR chemical shift of acidic proton is 13.1 ppm. This result indicates formation of H$^+$ (1-Bu—CB$_{11}$F$_{11}$) by the reduction of Ag$^+$ in the reaction of (PhAg) (1-Bu—CB$_{11}$F$_{11}$) with 10% H$_2$/N$_2$ at 135° C.

Example 38

This example illustrates the conductivity of polyfluorinated carborane in THF.

A calibrated Yellow Spring No. 3403 conductivity cell with a cell constant k=1.113 and a Model 31 conductivity bridge was employed. Measurements were done in the glove box with a purified nitrogen atmosphere. Conductivity of 0.0100 M THF solution of Cs(1-Me—CB$_{11}$F$_{11}$) was measured to be 1.47×10$^{-4}$ S/cm.

Example 39

To a mixture of 1.00 g of Cs(HCB$_{11}$H$_{11}$) in 50 mL of HF was added 300 psi of 10% F$_2$/N$_2$ in a 300 -mL Monel reaction vessel using the procedure of Example 2. The reaction mixture was warmed to room temperature and agitated for 24 h. The reaction mixture was cooled to about −78° C., placed under vacuum, and 290 psi of 10% F$_2$/N$_2$ was added. The mixture was again warmed to room temperature and agitated for 24 h. Excess gases were removed and a crude solid was dissolved in 100 mL of water. The aqueous solution was filtered and treated with an aqueous solution of Me$_3$NHCl (0.45 g). The white precipitate was filtered, washed with water and dried under vacuum to yield 1.08 g (74%) of (Me$_3$NH) (1-H—CB$_{11}$F$_{11}$)

Example 40

Same procedure as Example 39 was used except Bu$_4$NCl was used instead of Me$_3$NHCl to yield (Bu$_4$N) (1-H—CB$_{11}$F$_{11}$)

Example 41

About 0.55 g of (Me$_3$NH) (1-H—CB$_{11}$F$_{11}$) was added to 30 mL of 0.63 M aqueous NaOH solution. About 10 mL of water was removed from the mixture under vacuum. This procedure also removed trimethylamine from the mixture. To the resulting solution was added about 1.0 mL of dimethyl sulfate, and the mixture was stirred at room temperature for 1 h. The reaction solution was acidified to pH of about 1 with 1 M HCl solution and filtered. The filtrate was extracted with two 50 mL portions of ether. Organic layers were combined and concentrated to yield an oily white residue. The residue was dissolved in 20 mL of water and a large excess of Me$_3$NHCl in water was added. The white precipitate was filtered, washed with water and dried under vacuum to yield 0.47 g (82%) of (Me$_3$NH) (1-CH$_3$—CB$_{11}$F$_{11}$).

Example 42

A solution of 0.06 g of NaOH in 15 mL of water was added to about 0.37 g of (Me$_3$NH) (1-CH$_3$—CB$_{11}$F$_{11}$). About 5 mL of water was removed from the mixture under vacuum. This procedure also removed trimethylamine from the mixture. The resulting solution was acidified to pH of about 5 with 1 M HCl solution, and a solution of 0.25 g of CsCl in 5 mL of water was added. The mixture was cooled to 0° C., and the white solid was filtered, washed with cold water and dried to yield 0.39 g (90%) of Cs(1-CH$_3$—CB$_{11}$F$_{11}$).

Example 43

A mixture of 0.43 g of Cs(1-CH$_3$—CB$_{11}$F$_{11}$) and 1.2 g of AgNO3 in 150 mL of benzene was stirred at 70° C. for 24 h. The mixture was cooled to room temperature and filtered. The filtrate was concentrated and the resulting solid was recrystallized from 20 mL of dichloromethane to yield 0.42 g (87%) of (Ph)Ag(1-CH$_3$—CB$_{11}$F$_{11}$)

Example 44

A mixture of 0.30 g of (Ph)Ag(1-CH$_3$—CB$_{11}$F$_{11}$) and 0.18 g of Ph$_3$CCl in 30 mL of dichloromethane was stirred at room temperature for 1 h. The mixture was filtered, and the filtrate was concentrated to provide a yellow solid. The yellow solid was washed with isooctane to remove Ph$_3$CCl. The resulting solid was dried to yield 0.24 g (77%) of (Ph$_3$C)(1-CH$_3$—CB$_{11}$F$_{11}$)

Example 45

A mixture of 0.1 g of CuCl and 0.035 g of (Ph)Ag(1-Et—CB$_{11}$F$_{11}$) in dichloromethane was allowed to stand at room temperature for 1 month. Silver chloride was removed filtration, and the filtrate was treated with 1 atmosphere of CO. Cooling a saturated solution of Cu(1-Et—CB$_1$F$_{11}$) under 1 atmosphere of CO resulted in the formation of crystals of (CO)$_4$Cu(1-Et—CB$_{11}$F$_{11}$).

Example 46

Figure 3:
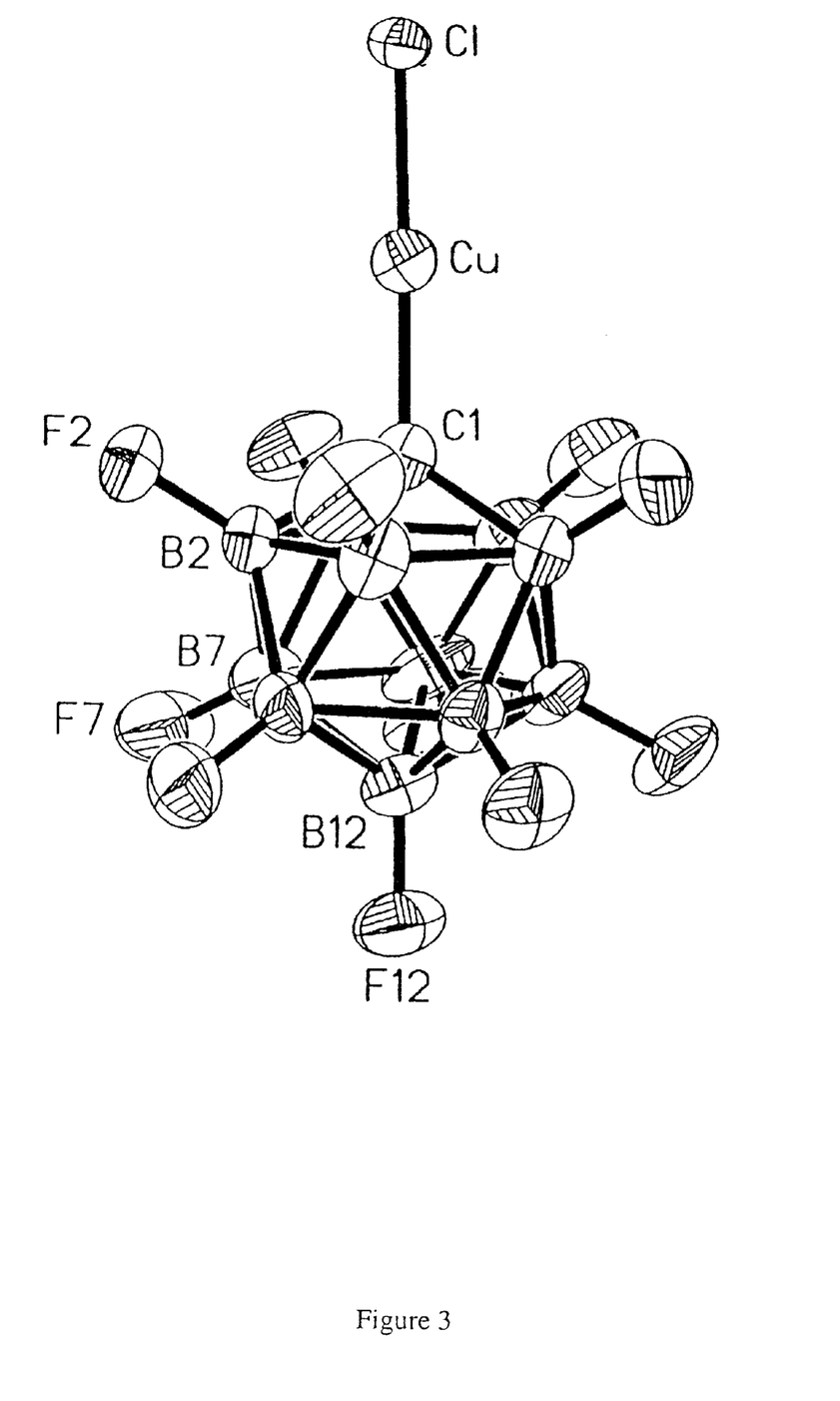
FIG. 3 is a x-ray crystal structure of $[ClCuCB_{11}F_{11}]^{-2}$.

A mixture of 0.13 g of Bu$_4$N(1-H—CB$_{11}$F$_{11}$), 0.061 g of Bu$_4$NCl and 0.041 g of [Cu(mesityl)]$_n$ in 10 mL of dichloromethane was stirred at room temperature for 0.5 h. The mixture was filtered, and the filtrate was concentrated to yield 0.17 g (85%) of (Bu$_4$N)$_2$(ClCuCB$_{11}$F$_{11}$). Diffraction quality crystal were grown from acetonitrile, and the x-ray crystal structure is shown in FIG. 3.

Example 47

To a solution of 0.52 g of (Me$_3$NH)AsB$_{11}$H$_{11}$ in 15 mL of THF was added 4 mL of 2.0 M n-BuLi in hexane solution. The reaction mixture was stirred for 10 minutes and about ½ of THF was removed under vacuum. The remaining tan, cloudy mixture was cooled to 0° C., and 3.8 mL of BF$_3$·OEt$_2$ was added. The resulting mixture was stirred overnight. The mixture was concentrated and dissolved in 1 M NaOH. A large excess of Me$_3$NHCl was added to the aqueous solution, and the resulting solid precipitate was filtered and dried to yield (Me$_3$NH) (2-F—AsB$_{11}$H$_{10}$). $^{11}$B NMR (acetone-d6, δ): 15.8 (s), 4.6 (d), −6.9 (d), −8.7 (d), −11.3 (d) and −17.8 (d). $^{19}$F NMR. −192.7 (q, J$_{B\text{-}F}$=78 Hz).

Example 48

About 7 mL of HF was added to a Monel reaction vessel containing about 20 mg of Cs(AsB$_{11}$H$_{11}$), and the resulting solution was stirred at 200° C. for 64 h. HF was removed via a vacuum transfer technique, and the sample was dried under vacuum. NIEMS showed the presence of Cs(AsB$_{11}$H$_{11}$), Cs(AsB$_{11}$H$_7$F$_4$), and Cs(AsB$_{11}$H$_6$F$_5$) in the ratio of about 1:7:2, respectively. NIEMS (m/z): 205.2 (F$_0$, 10%), 277.2 (F$_4$, 70%) and 295.2 (F$_5$, 20%).

Example 49

About 9 mL of HF was added to a Monel reaction vessel containing about 18.8 mg of Cs(SbB$_{11}$H$_{11}$), and the resulting solution was stirred at room temperature for 44 h. HF was removed via a vacuum transfer technique, and the sample was dried under vacuum. NIEMS showed the presence of Cs(SbB$_{11}$H$_{11}$), Cs(SbB$_{11}$H$_{10}$F), Cs(SbB$_{11}$H$_9$F$_2$), and Cs(AsB$_{11}$H$_8$F$_3$) in the ratio of about 1:1:97:1, respectively. Cs(SbB$_{11}$H$_9$F$_2$): $^{11}$B NMR (acetone-d6, δ): 13.1 (s), 7.7 (d), −11.2 (d), −14.1 (d), −17.3 (d), and −19.0 (d). $^{19}$F NMR: 194.1 (q). NIEMS (m/z): 252.2 (F$_0$), 269.2 (F$_1$), 287.3 (F$_2$), and 305.3 (F$_3$).

Example 50

About 9 mL of HF was added to a Monel reaction vessel containing about 22.6 mg of Cs(BiB$_{11}$H$_{11}$), and the resulting solution was stirred at room temperature for 44 h. HF was removed via a vacuum transfer technique, and the sample was dried under vacuum. NIEMS showed the presence of Cs(BiB$_{11}$H$_{11}$), Cs(BiB$_{11}$H$_{10}$F), Cs(BiB$_{11}$H$_9$F$_2$), Cs(BiB$_{11}$H$_8$F$_3$), and Cs(BiB$_{11}$H$_8$F$_4$). NIEMS (m/z): 339.4 (F$_0$), 357.5 (F$_1$), 375.5 (F$_2$), 392.5 (F$_3$), and 410.5 (F$_4$), and 428.4 (F$_5$).

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A compound comprising a polyhalogenated monoheteroborane anion of the formula R$_a$ZB$_b$H$_c$F$_d$X$_e$(OR")$_f^{-1}$ whose core structure contains one non-boron atom Z, wherein R is bonded to Z and H, F, X and OR" are bonded to boron atoms, and wherein R is selected from the group consisting of polymer, hydrogen, halide, C$_1$–C$_{10}$ alkyl, C$_1$–C$_{10}$ cycloalkyl, C$_1$–C$_{10}$ alkenyl, C$_1$–C$_{10}$ alkynyl, and C$_4$–C$_{20}$ aryl, wherein said polymer is selected from the group consisting of polyethylene glycol, polyethylene, polypropylene, and polystyrene;

Z is selected from the group consisting of C, Si, Ge, Sn, Pb, N, P, As, Sb, and Bi;

each X is independently halide;

R" is selected from the group consisting of polymer, hydrogen, C$_1$–C$_{10}$ alkyl, C$_1$–C$_{10}$ cycloalkyl, C$_1$–C$_{10}$ alkenyl, C$_1$–C$_{10}$ alkynyl, and C$_4$–C$_{20}$ aryl, wherein said polymer is selected from the group consisting of polyethylene glycol, polyethylene, polypropylene, and polystyrene;

a is 0 or 1;

b is an integer from 5 to 13;

c is an integer from 0 to 12;

d is an integer from 2 to 13;

e is an integer from 0 to 11; and f is an integer from 0 to 5.

2. The compound of claim 1, wherein X is selected from the group consisting of chloride, iodide and bromide.

3. The compound of claim 1, wherein Z is selected from the group consisting of C, Si, P, and N.

4. The compound of claim 3, wherein Z is C and R" is hydrogen.

5. The compound of claim 4, wherein a is 1.

6. The compound of claim 5, wherein R is selected from the group consisting of hydrogen, halogen, and $C_1$–$C_{10}$ alkyl.

7. The compound of claim 6, wherein R is selected from the group consisting of hydrogen, fluoride, methyl, trifluoromethyl, vinyl, ethyl, butyl, fluoromethyl, difluoromethyl and propyl.

8. The compound of claim 7, wherein R is hydrogen.

9. The compound of claim 8, wherein b is 11, and c and e are 0.

10. The compound of claim 9, wherein d is 11 and f is 0.

11. The compound of claim 9, wherein d is 10 and f is 1.

12. The compound of claim 9, wherein d is 9 and f is 2.

13. The compound of claim 8, wherein b is 11, c is 1, d is 10, and e and f are 0.

14. The compound of claim 8, wherein b and d are 9, and c, e and f are 0.

15. The compound of claim 7, wherein R is methyl.

16. The compound of claim 15, wherein b and d are 11, and c, e and f are 0.

17. The compound of claim 7, wherein R is ethyl, b and d are 11, and c, e and f are 0.

18. The compound of claim 7, wherein R is trifluoromethyl, b and d are 11, and c, e and f are 0.

19. The compound of claim 7, wherein R is fluoride, b is 11, d is 11, and c, e and f are 0.

20. The compound of claim 1, further comprising a counter cation, wherein said counter cation is selected from the group consisting of hydrogen, sodium, ammonium, lithium, cesium, trityl, tetraalkyl ammonium and tetraphenyl phosphonium.

21. The compound of claim 20, wherein said counter cation is lithium.

22. A solution comprising the polyhalogenated monoheteroborane anion of claim 1.

23. A gel comprising the polyhalogenated monoheteroborane anion of claim 1.

24. The gel of claim 23 further comprising a polymer.

25. A molten salt comprising the polyhalogenated monoheteroborane anion of claim 1.

26. A liquid comprising the polyhalogenated monoheteroborane anion of claim 1.

* * * * *

UNITED STATES PATENT AND TRADEMARK OFFICE
CERTIFICATE OF CORRECTION

PATENT NO.   : 6,130,357
DATED        : October 10, 2000
INVENTOR(S)  : Steven H. Stauss, Sergei V. Ivanov and Anthony J. Lupinetti It is certified that error appears in the above-identified patent and that said Letters Patent is hereby corrected as shown below:

Column 1,
Line 8, please add:

-- STATEMENT REGARDING FEDERALLY SPONSORED RESEARCH

The U.S. Government has a paid-up license in this invention and the right in limited circumstances to require the patent owner to license others on reasonable terms as provided for by the terms of Grant No. CHE-9628769 awarded by the National Science Foundation. --

Signed and Sealed this

Twenty-eighth Day of January, 2003

JAMES E. ROGAN
*Director of the United States Patent and Trademark Office*